United States Patent [19]

Bhattacharya et al.

[11] Patent Number: 5,237,061

[45] Date of Patent: Aug. 17, 1993

[54] METHODS OF SYNTHESIZING BENIGN PROSTATIC HYPERTROPIC AGENTS AND THEIR INTERMEDIATES

[75] Inventors: Apurba Bhattacharya, Rahway; Ulf H. Dolling, Westfield, both of N.J.; Joseph S. Amato, Brooklyn, N.Y.; John M. Williams, Somerset, N.J.

[73] Assignee: Merck & Co., Inc., Rahway, N.J.

[21] Appl. No.: 264,652

[22] Filed: Oct. 31, 1988

[51] Int. Cl.$^5$ .................. C07J 75/00; C07J 73/00
[52] U.S. Cl. .................. 544/125; 544/361; 546/77; 540/108
[58] Field of Search .................. 546/77; 540/108; 552/544; 544/361, 125

[56] References Cited

U.S. PATENT DOCUMENTS

| | | | |
|---|---|---|---|
| 4,179,453 | 12/1979 | Johnston | 260/397.1 |
| 4,197,308 | 4/1980 | Szmuszkovicz | 546/205 X |
| 4,220,775 | 7/1980 | Rasmusson et al. | 546/77 |
| 4,249,001 | 2/1981 | Wenger | 542/404 |
| 4,377,584 | 3/1983 | Rasmusson et al. | 546/77 |
| 4,460,509 | 7/1984 | Mosbach et al. | 540/108 |
| 4,602,099 | 7/1986 | Parker | 549/479 |
| 4,689,410 | 8/1987 | Barton et al. | 540/108 |
| 4,760,071 | 7/1988 | Rasmusson et al. | 514/284 |
| 4,859,681 | 8/1989 | Rasmusson et al. | 514/284 |

FOREIGN PATENT DOCUMENTS 0155096  9/1985  European Pat. Off. .

OTHER PUBLICATIONS

Parker, Chemical Abstracts, vol. 89: 109057n (1978).
Suzuki, et al., Chemical Abstracts, vol. 102:203785g (1985).
Shealy, et al., Chemical Abstracts, vol. 101: 130921r (1984).
Fieser, et al., "Advanced Organic Chemistry", Reinhold Publishing Co., New York, (1961) pp. 114–118.
Prasad, et al., J. of Labelled Compounds & Radiopharmaceuticals, vol. 22(4), pp. 353–358 (1985).
Locurio, et al., Tetrahedron, vol. 44, No. 1, pp. 35–40 (Jan. 1988).
Fieser, et al., "Reagents for Organic Synthesis", John Wiley & Sons, Inc., (1967) pp. 415–424.
Brooks, et al., C—Acylation Under Virtually Neutral Conditions, Angew, Chem. Int. Ed. Engl. 18(1979) No. 1, pp. 72–74.
Rasmusson, et al., Azasteroids ad Inhibitors of Rat Prostatic 5 alpha-Reductose, J. Med. Chem. 1984, 27, pp. 1690–1701.
Rasmusson, et al., Azasteroids: Structure-Activity Relationships for Inhibition of 5 Alpha-Reductase and of Androgen Receptor Binding, J. Med. Chem. 1986, 29, 2298–2315.
Bhattacharya, et al., Silylation-Mediated Oxidation of 4-Aza-30 Ketosteroids with DDZ Proceeds via DDZ-Substrate Adducts, J. Am. Chem. Soc., vol. 110, No. 10, 1988, 3318–19.

*Primary Examiner*—Mukund J. Shah
*Assistant Examiner*—E. C. Ward
*Attorney, Agent, or Firm*—Charles M. Caruso

[57] ABSTRACT

A process for preparing compounds of the formula

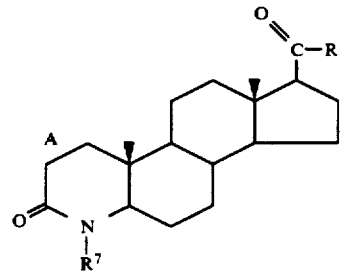

which comprises reacting an imidazolide of the formula

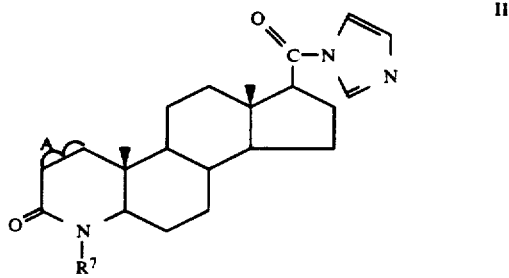

with an amine of the formula NHR$_4$R$_5$ in the presence of a Grignard reagent to form a compound of formula I or reacting an imidazolide of formula II with a compound of the formula R$_6$Mgx to form a compound of formula I.

2 Claims, No Drawings

METHODS OF SYNTHESIZING BENIGN PROSTATIC HYPERTROPIC AGENTS AND THEIR INTERMEDIATES

BACKGROUND OF THE INVENTION

This invention is concerned with a process for preparing 17β substituted 3-oxo-4 azasteroids by utilizing an imidazolide as a common intermediate from which these azasteroids may be formed.

Heretofore 17β substituted 3-oxo-4 azasteroids have been produced by using different synthetic processes for each azasteroid.

European Patent Application 85301122.9 discusses the synthesis of 17 substituted 3-oxo-4-azasteroids. This process consists of the formation of a 17β (2-pyridylthiocarbonyl)3-oxo-4-azasteroid which can be substituted at the four position and can have a double bond at the 1,2 positions. This compound is then reacted with a substituted amine to form the corresponding 17β (N-carbamoyl)3-oxo-4-azasteroid, or it can be reacted with a Grignard reagent to form a 17β acyl-3-oxo-4-azasteroid. While this process is feasible, it has the disadvantage of requiring chromatography to obtain the final product.

Rasmusson et. al., J. Med. Chem. 1986, 29, 2298-2315 also discusses the synthesis of 17β 3-oxo-4-azasteroids by reacting a 17β carboxy-androstan-3-one with an acid chloride, which activates the 17β carboxy functionality and forms the corresponding 17β carboxychloro compound, followed by treatment with an amine to form the 17β amido analog. This product is then treated with an oxidizing agent and an amine to introduce a nitrogen into the A ring of the steroid to form the 17β substituted-3-oxo-4-azasteroid. The disadvantage of this process is that the nitrogen cannot be introduced into the A ring of the steroid until after the amination of the 17β carboxychloro since the lactam ring formed would interfere with the acid chloride activation. See also U.S. Pat. Nos. 4,220,775 and 4,377,584 which discuss the synthesis of 17β substituted 3-oxo-4-azasteroids.

The 17β substituted 3-oxo-4-azasteroids formed by the process of the present invention may also contain a double bond between the 1,2 positions of the A ring of the azasteroid. This double bond can be introduced into the azasteroid at any point during the process of the present invention. This includes prior to the formation of the imidazolide, after the imidazolide formation, or after the introduction of the 17β ketone or amide. The 1,2 double bond introduction is well known in the art. See Back, T. G., J. Org. Chem. 46: 1442 (1981); and Rasmussen et. al., J. Med. Chem. 29, 2298 (1986).

The imidazolide formation, which is part of the present invention, is necessary in order to activate the 17β carboxylic acid functionality of the 3-oxo-4-azasteroid. The formation of an imidazolide and its use as an intermediate to form other compounds is known in the art. See Brooks et. al., Angew. Chem. Int. Ed. Engl., 18 (1979) No. 1. Brooks et. al. discusses the use of an imidazolide intermediate in ketone formation. However, there is no discussion of the use of an imidazolide intermediate in the formation of an amide, such as is disclosed in the present invention. Also, it has not been known heretofore to utilize an imidazolide intermediate in the synthesis of 3-oxo-4-azasteroids.

The process of the present invention provides for the synthesis of an imidazolide which is used as a common intermediate from which various 17β substituted 3-oxo-4-azasteroids may be formed. This avoids the multistep procedures and the use of chromatography associated with the prior art.

SUMMARY OF THE INVENTION

The present invention provides for the synthesis of 17β substituted 3-oxo-4-azasteroids by utilizing an imidazolide as a common intermediate. Thus the present invention provides a method for preparing a compound of the formula

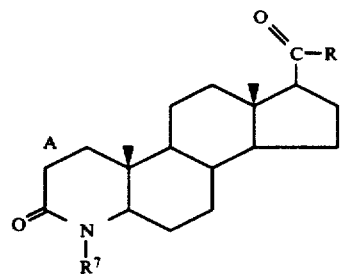

wherein
R is
 (i) a straight or branched chain alkyl group having 1 to 12 carbons,
 (ii) a straight or branched chain alkyl group having 1 to 12 carbons in which a hydrogen is substituted with a hydroxy, carboxylic acid or an alkyl ester having 1 to 4 carbons,
 (iii) a cycloalkyl group having 3 to 6 carbons,
 (iv) phenyl,
 (v) $OR^1$, where $R^1$ is hydrogen or alkali metal, a $C_{1-18}$ straight or branched chain alkyl group or benzyl;
 (vi) $NR^2R^3$, where $R^2$ and $R^3$ are each independently selected from hydrogen; $C_{1-12}$ straight or branched chain alkyl; $C_{1-12}$ straight or branched alkyl having a hydrogen substituted with a hydroxy, carboxylic acid or $C_{1-4}$alkyl ester; $C_{3-1}$ cycloalkyl; phenyl; or $R^2$ and $R^3$ taken together with with the nitrogen to which they are attached represent a 5-6 member saturated ring comprising up to one other heteroatom selected form oxygen and nitrogen;
$R_7$ is hydrogen, methyl or ethyl; and
A is
 (1) —CH₂—CH₂—
 (2) —CH=CH—
which comprises reacting an imidazolide of the formula

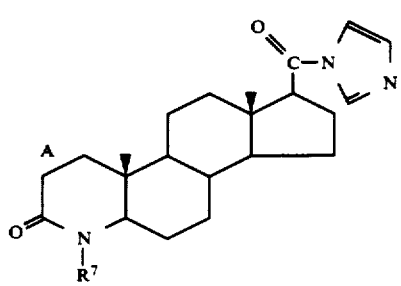

wherein
A and $R^7$ are as previously defined, with a compound of the formula $NHR^4R^5$ in the presence of a Grignard reagent or, reacting the compound of formula II with a compound of the formula $R^6MgX$ wherein $R^4$ and $R^5$ are independently selected from the group consisting of hydrogen; $C_{1-12}$ straight or branched chain alkyl; $C_{1-12}$ straight or branched chain alkyl having a hydrogen substituted with a hydroxy, carboxylic acid or $C_{1-4}$ alkyl ester; $C_{3-10}$ cycloalkyl; phenyl; or $R^4$ and $R^5$ taken together with the nitrogen to which they are attached represent a 5-6 member saturated ring comprising up to one other heteroatom selected from oxygen and nitrogen;

$R_6$ is
(1) a straight or branched chain alkyl group group having 1-12 carbons;
(2) a straight or branched chain alkyl group having 1 to 12 carbons in which a hydrogen is substituted with a hydroxy, carboxylic acid or an alkyl ester having 1 to 4 carbons
(3) a cycloalkyl group having 3 to 6 carbons;
(4) phenyl;
(5) $OR^7$, where $R^7$ is hydrogen, a alkali metal, a $C_{1-18}$ straight or branch chain alkyl group, or benzyl; and X is a halogen selected from the group consisting of chlorine, bromine and iodine.

Novel imidazolide compounds useful in preparing the corresponding 17β substituted 3-oxo-4-azasteroids are also an important part of the present invention, as is the process for preparing these imidazolides.

The azasteroid compounds prepared by the processes of the present invention are testosterone-5α reductase inhibitors useful for treating the hyperandrogenic conditions of acne vulgaris, seborrhea, female hirsitism, androgenic alopecia, including male pattern alopecia, prostatic carcinoma and benign prostatic hypertrophy by topical or systemic administration.

DETAILED DESCRIPTION OF THE INVENTION

Generally, the process of the present invention involves reacting an imidazolide with a carbon nucleophilic group with or without the presence of an iron catalyst to produce a 17,β keto 3-oxo-4-azasteroid. In the alternative the imidazolide is reacted with a nitrogen nucleophilic group, with prior activation of the nitrogen neucleophile by a Grignard reagent, to produce a 17β amido 3-oxo-4-azasteroid.

The carbon nucleophilic group is a Grignard reagent of the formula $R_6MgX$, where $R_6$ is as previously defined and X is chlorine, bromine, or iodine. The reaction scheme for the ketonization of the imidazolide can be represented as follows:

2)

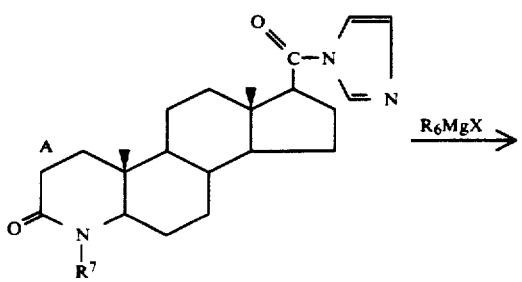

-continued

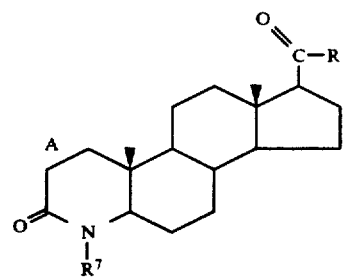

If a Grignard reagent containing a β hydrogen is employed in the ketonization of the imidazolide there may be secondary alcohol formation. This is caused by a hydride transfer from the β hydrogen of the Grignard reagent. This secondary alcohol formation can be minimized by the use of an iron catalyst such as $FeCl_3$ or iron acetylacetonate. If no β hydrogen is present in the $R_6$ group of the Grignard reagent then there is no risk of secondary alcohol formation and the iron catalyst is not needed.

The nitrogen nucleophilic group is represented by a substituted amine of the formula $NHR_4R_5$ wherein $R_4$ and $R_5$ are as previously defined. The substituted amine must be activated via reacting it with a Grignard reagent of the formula $R_6MgX$ wherein $R_6$ is previously defined and X is chlorine, bromine or iodine. This results in the formation of a substituted aminomagnesium halide compound of the formula $NR_4R_5MgX$. The activation of the substituted amine by formation of the substituted aminomagnesium halide compound is necessary in order to form the amide linkage between the imidazolide and the substituted amine. After the substituted amine is activated it is reacted with the imidazolide to form the corresponding 17β amids 3-oxo-4-azasteroid. The reaction scheme can be represented as follows:

1)

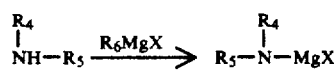

2)

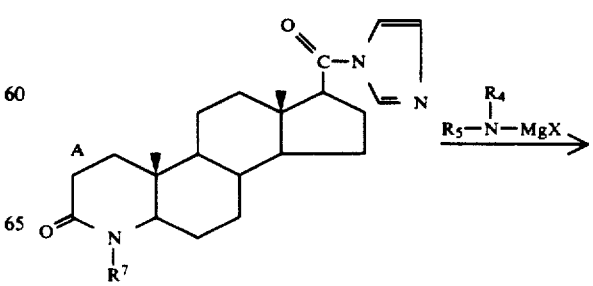

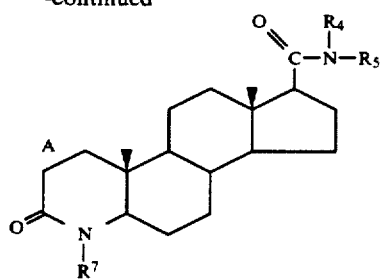

The novel imidazolide intermediates formed in the process disclosed herein is also significant part of the present invention. The imidazolide intermediates are compounds of the formula:

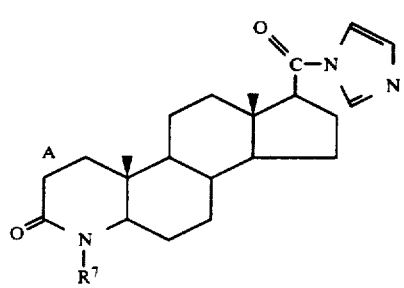

wherein:
R[7] is hydrogen, methyl or ethyl; and
A is
(1) —CH$_2$—CH$_2$—
(2) —CH=CH—.

The novel imidazolide intermediates may be formed via either of two methods.

In the first method of synthesis, a 17β carboxy-3-oxo-4-substituted-4-aza-androstan-3-one or the corresponding Δ[1] unsaturated version, is reacted with a carbonyl diimidazole to form the imidazolide intermediate. The reaction scheme can be represented as follows:

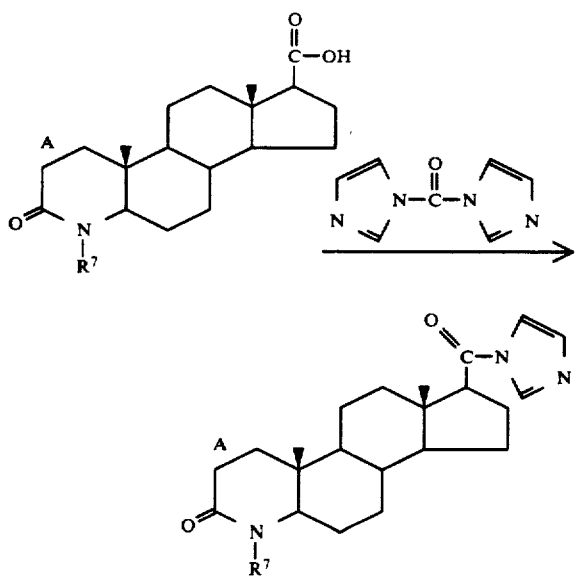

wherein R[7] and A are previously defined.

The carbonyl diimidazole and 17β carboxy-4-substituted-4-aza-androstan-3-one or the corresponding Δ[1] unsaturated version are readily available starting materials or can be synthesized by processes known in the art.

In the alternative, the imidazolide may be formed by reacting a 17β carboxy-4-substituted-4-aza-androstan-3-one or the coresponding Δ[1] unsaturated version, with sulfonyl diimidazole. The azasteroid is a readily available starting material, however the sulfonyl diimidazole must be synthesized by reacting an imidazole with thionyl chloride. The reaction scheme for the above described synthesis is as follows

1)

2)

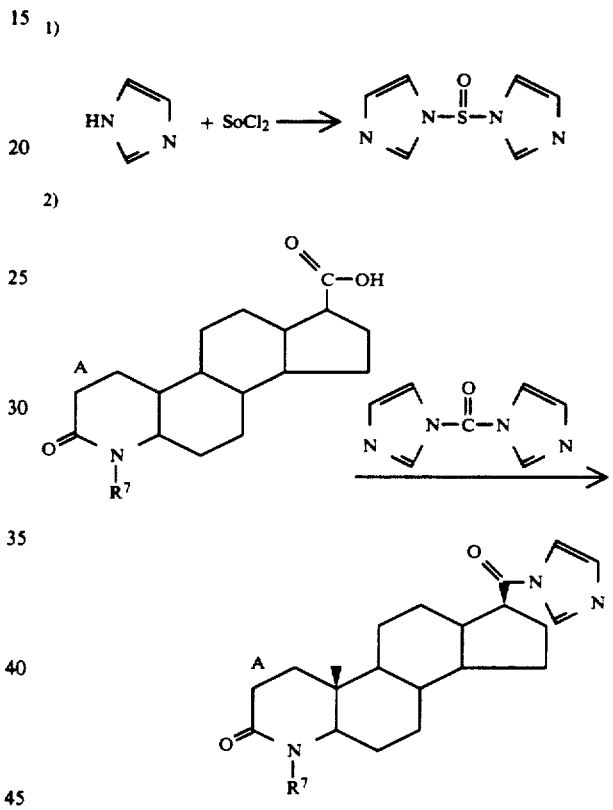

In one embodiment of the present invention 1-[[(5α, 17β)-3-oxo-4-azaandrost-1-en-17-yl] carbonyl]-1-H imidazole is reacted with tert-butylamine in the presence of ethylmagnesium bromide to form N-(1,1-dimethylethyl)-3-oxo-4-aza-5α-androst-1-ene-17β-carboxamide, a preferred compound of the present invention.

In another embodiment of the present invention 1-[[(5α, 17β)-3-oxo-4-azaandrost-1-en-17yl] carbonyl]-1H imidazole is reacted with isobutylmagnesium chloride in the presence of ferric chloride to form 23-methyl-4-aza-21-nor-5α-chol-1-ene-3,20-dione another preferred compound of the present invention.

The following examples should be considered as not limiting the invention and will serve to illustrate the manner in which the present invention is accomplished.

EXAMPLE 1

1-[[(5α, 17β)-3-oxo-4-azaandrost-1-en-17yl] carbonyl]-1H imidazole

A 3 L three-necked flask equipped with a nitrogen inlet, overhead stirrer, and internal thermocouple was charged with 300.0 g of 3-oxo-4-aza-5α-androst-1-ene- 17β-carboxylic acid and 1800 mL of dichloromethane. Carbonyldiimidazole (160.8 g) was added in 20 g portions over 20 min.

The reaction appears to be autocatalyzed by the imidazole produced and no evidence of reaction is noted for several minutes after addition is begun. As the reaction proceeds, the solids gradually dissolve, and the resulting solution is deep amber in color. Gas evolution is observed but does not prove to be a problem at the recommended rate of addition. Only a slight increase in temperature (ca 2° C.) is observed during the addition.

After the addition had been completed the mixture was aged for 20 minutes and then concentrated under atmospheric pressure to ca. 1 L. While continuing to remove dichloromethane, tetrahydrofuran was added via addition funnel at a rate which maintained the volume at 1 L. After 1500 mL of tetrahydrofuran had been added, a constant distillation temperature of 65° C. was obtained, and the mixture was allowed to cool to room temperature and was stirred overnight. The product was isolated by filtration under a flow of nitrogen washing the filter cake with two 160 mL portions of tethydrofuran. Drying at 60° C. under a flow of nitrogen afforded a 304.8 g of tan solid which proved to be 100 wt % pure (91.5% yield).

Completion of the reaction was determined by liquid chromatography assay. The tethydrofuran was dried over 4 Å molecular sieves (KF=27 μg/mL). The volume of the filter cake was ca. 600 mL.

EXAMPLE 2

1-[[(5α, 17β)-3-oxo-4-azaandrost-1-en-17-yl]carbonyl]-1H imidazole 1 gram of imidazole was dissolved in 6 mL's of tetrahydrofuran. To this solution was added a solution of $SOCL_2$ (0.43 g) in 4 mL's of tetrahydrofuran with stirring under nitrogen for 1 hour. The precipitated imidazole hydrochloride was filtered under nitrogen and the filtrate was added to a suspension of 0.319 g of 3-oxo-4-aza-5α-androst-1-ene-17β carboxylic acid in 2 mL's of tetrahydrofuran. The mixture was stirred under nitrogen at 20° C. for 1 hour and filtered to produce 0.294 g of the imidazolide.

EXAMPLE 3

23-methyl-4-aza-21-nor-5α-chol-1-ene-3,20-dione

A 0.02M solution of ferric chloride in tetrahydrofuran was prepared by adding 1.6 g of anhydrous ferric chloride to 500 mL of tetrahydrofuran followed by 16 g of 4 Å molecular sieves. The mixture was allowed to stand overnight before using. A 1 L three-necked flask equipped with a 125 mL addition funnel, overhead stirrer, nitrogen inlet, and internal thermocouple was charged with 375 mL of 0.02M ferric chloride in tetrahydrofuran and 25.0 g of 3-oxo-4-aza-5α-androst-1-ene-17β-carboxylic acid. The resulting slurry was stirred and cooled to −10° C. using a dry ice/acetone bath. A 2.0M solution of isobutylmagnesium chloride (85.1 mL, 2.5 molar equivalents) was added via addition funnel over 25 min maintaining the internal temperature below −6° C. The temperature rises most during the initial stages of the addition possibly due to rapid deprotonation of the lactam. More rapid addition is possible once the first 25 mL of isobutylmagnesium chloride is added.

After the addition was completed the mixture was aged at −10° C. for 1.5 h and additional isobutylmagnesium chloride (17.0 mL, 0.5 molar equivalents) was added. The reaction was greater than 99% complete as noted by liquid chromatography after 45 minutes, and the reaction was quenched by rapidly siphoning the mixture into 250 mL of vigorously stirred 2 N HCl cooled to 0° C. The mixture was warmed to room temperature and stirred overnight under nitrogen. Filtration (120 mL medium sintered glass funnel) washing with 30 mL of 2 N HCL and drying in a stream of air for 1 hour afforded 23.9 g of a white solid which was 87% product by liquid chromatography assay (20.8 g, 86% assay yield.)

Liquid chromatography assay of the filtrate (aqueous and organic solutions) and HCl wash showed 1.1% loss of product.

The solid was dissolved in 100 mL of hot acid and the volume was reduced under a stream of nitrogen until the solution was saturated (ca. 80 mL). The stirred solution was allowed to cool slowly to room temperature and age overnight. Filtration (60 mL medium sintered glass funnel) washing with 0.5 bed volumes each of acetic acid and 20% aqueous acetic acid afforded an off white crystalline solid which was dried under a stream of air for 1 hour then at 40°-50° C. under a nitrogen sweep to give 14.3 of steroidal ketone (59.5% yield, 97.1% pure).

EXAMPLE 4

(5α, 17β)-17-(2-methyl-1-oxopropyl)-4-aza-androst-1-ene-3-one

A 1 L three-necked flask equipped with a 125 mL addition funnel, overhead stirrer, nitrogen inlet, and internal thermocouple was charged with 500 mL of tetrahydrofuran and 25.0 g of 3-oxo-4-aza-5α-androst-1-ene-17β-carboxylic acid. The resulting slurry was stirred and cooled to −35° C. using a dry ice/acetone bath. A 2.0M solution of isopropyl-magnesium chloride (85.1 mL, 2.5 molar equivalents) was added via addition funnel over 25 minutes maintaining the internal temperature below −33° C. The temperature rises most during the initial stages of the addition possibly due to rapid deprotonation of the lactam. More rapid addition is possible once first ca. 25 mL of isobutylmagnesium chloride is added.

After the addition was completed the mixture was aged at −33° to −37° C. for 1.5 hours and additional isopropylmagnesium chloride (17.0 mL, 0.5 molar equivalents) was added. After warming slowly to 0° over 1 hour and aging for 30 minutes, the reaction was greater than 99% complete as noted by liquid chromatography, and the reaction was quenched by rapidly siphoning the mixture into 250 mL of vigorously stirred 2 N HCl cooled to 0° C.

Sodium chloride (17 g) was added, and the resulting mixture was warmed to room temperature and stirred overnight under nitrogen. The mixture was poured into a separatory funnel and allowed to settle for 2 hours before separating the layers. The organic solution was filtered through a medium sintered glass funnel and was concentrated to 150 mL by atmospheric distillation. Acetic acid (100 mL) was added at a rate which maintained the volume at 150 mL and concentration was continued to a volume of 80 mL. After cooling to 100° C., water (20 mL) was added over 10 min, and the mixture was allowed to cool slowly to room temperature and age overnight.

Filtration (60 mL sintered glass funnel) washing with two bed volumes of 40% aqueous acetic acid and drying at 140° C. and ca. 1 mm Hg for 20 hours afforded 17.5 g of an off white crystalline solid (74.6% yield, 98.7% pure).

EXAMPLE 5

N-(1,1-dimethylethyl)-3-oxo-4-aza-5α-androst-1-ene-17β-carboxamide

A three-neck round bottom flask equipped with $N_2$ inlet, reflux condenser, addition funnel and overhead stirrer was charged with 12 g of $\Delta^1$ imidazolide (from Example 1 or 2) and 360 mL tetrahydrofuran. The slurry was cooled to 0° C. and to it via addition funnel tert-butylamine (12.1 mL, 115.6 mmol) was added. A solution of ethylmagnesium bromide in tetrahydrofuran (56.2 mL, 2.0M, 112.4 mmol) was added over ten minutes. The pot temperature was observed to increase to 10° C. during the addition. The mixture was heated at reflux for 5.5 hours (contains <0.1 area % starting material) then cooled to room temperature and saturated aqueous ammonium chloride (320 mL) was added. The temperature during the quench rose to 34° C.

After cooling to 25° C., 30 mL of water was added to dissolve the inorganic salts. The mixture was poured into a separatory funnel and allowed to settle for 1 hour before separating the layers. Liquid chromatography assay (442 mL solution, 2.0 mL diluted to 100 mL) indicated that 11.24 g of product (97.6 area % pure) was present in the tetrahydrofuran solution while only a trace (18 mg) of product remained in the aqueous layer (400 mL, 10 mL diluted to 100 mL with HOAc, water, and acetonitrile). The tetrahydrofuran solution was concentrated on a rotary evaporator to 200 mL, and the result was diluted with 200 mL of dichloromethane. This solution was washed with 200 mL of 2 N HCl in a separatory funnel. After setting for 15 minutes, the layers were separated and assayed as before. The organic solution contained 11.30 g of product (101% recovery) while the aqueous layer contained no detectable product. The organic solution was concentrated to 40 mL under nitrogen at atmospheric pressure in a 250 mL three-necked flask equipped with an overhead stirrer, addition funnel, and distillation head. The final bath temperature was 100° C. and the vapor temperature was 65° C. Ethyl acetate (60 mL, dried over 4 Å molecular sieves, KF=35 μg/mL) was added and distillation was continued adding ethyl acetate to maintain a constant still volume of 100 mL. After 180 mL had been added, there remained less than 0.4 area % tetrahydrofuran in the distillate by GC analysis (DB-1 15 m×0.25 mm, film thickness 1.0 micron, JSW serial #82804, oven 80° C., injector 250° C., 4 psi, ethyl acetate: 3.44 min; THF: 3.76 min). The volume was decreased to 50 mL and an additional 60 mL of ethyl acetate was added and volume reduced to 40 mL. The mixture was cooled to room temperature over 20 minutes (KF=132 μg/mL) and then at 0° C. for 1 hour before filtering (60 mL medium sintered glass funnel) under nitrogen. The filter cake was washed with 20 mL of cold dry ethyl acetate and 10 mL of hexane. The resulting white solid was dried at 60° C. with a nitrogen purge overnight to give 9.53 g of Product (97.4% pure relative to standard, 99.9 area % pure, 83% yield).

EXAMPLE 6

22(RS)-methyl-4-aza-21-nor-5α-chol-1-ene-3,20-dione 22.5 g of 1-[[(5α, 17β)-3-oxo-4-azaandrost-1-ene-17-yl]-carbonyl]-1H. Imidazole (96% pure) was suspended in 100 mLs of tetrahydrofuran and was cooled to −40° and 150 mLs of 2M, solution of sec-butyl magnesium chloride in ether was added rapidly keeping the reacting temperature below −30° C. with dry ice/methanol bath. Then the reaction mixture temperature was raised to −15° C. Then 300 mL 0.02M Fe(acac)$_3$/tetrahydrofuran solution was added over 20 minutes keeping the temperature between −12° and −16° C. 10 minutes after addition was complete a liquid chromatography sample showed 22.4 area % product, 0.2 area % imidazolide. The reaction mixture was quenched into a cold (0° C.) stirred mixture of 230 mL $CH_2CL_2$, 230 mL 2N HCL over a 10 minute period. The temperature rose to 15° C. The bottom aqueous layer was separated (300 mL). The organic layer (895 mL) contained by liquid chromatography assay 12.6 g of ketone. The organic layer was washed with 230 mL 1M $NaHCO_3$, 230 mLs 2N HCL and 230 mL $H_2O$. The organic layer (780 mL) contained 12.3 g of product by liquid chromatography (yield 58.3%). The product was crystalized by turning over the solvent to ethyl acetate via distillation with 80% recovery.

What is claimed is:

1. A method for preparing a compound of the formula:

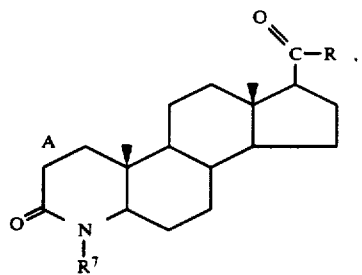

wherein

R is (i) a straight or branched chain alkyl group having 1 to 12 carbons, (ii) a straight or branched chain alkyl group having 1 to 12 carbons in which a hydrogen is substituted with a hydroxy, carboxylic acid or an alkyl ester having 1 to 4 carbons, (iii) a cycloalkyl group having 3 to 6 carbons, (iv) phenyl, (v) OR$^1$, where R$^1$ is hydrogen or alkali metal, a $C_{1-18}$ straight or branched chain alkyl group or benzyl;

(vi) NR$^2$R$^3$ where R$^2$ and R$^3$ are each independently selected from hydrogen; $C_{1-12}$ straight or branched chain alkyl; $C_{1-12}$ straight or branched alkyl having a hydrogen substituted with a hydroxy, carboxylic acid or $C_{1-4}$ alkyl ester; $C_{3-10}$ cycloalkyl; phenyl; or R$^2$ and R$^3$, taken together with the nitrogen to which they are attached represent a 5-6 member saturated ring comprising up to one other heteroatom selected from oxygen and nitrogen;

R$_7$ hydrogen, methyl, or ethyl;

A is
(1) —CH$_2$—CH$_2$—
(2) CH=CH—;
which comprises reacting an imidazolide of the formula:

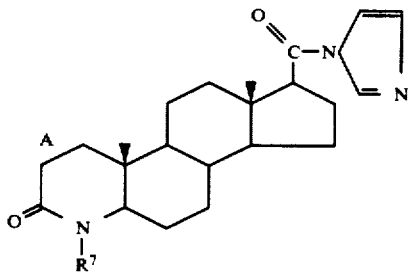

II with a compound of the formula NHR$^4$R$^5$ in the presence of a Grignard reagent or, reacting the compound of formula II with a compound of the formula R$^6$MgX wherein R$^4$ and R$^5$ are independently selected from the group consisting of hydrogen; C$_{1-12}$ straight or branched chain alkyl; C$_{1-12}$ straight or branched chain alkyl having a hydrogen substituted with a hydroxy, carboxylic acid or C$_{1-4}$ alkyl ester; C$_{3-10}$ cycloalkyl; phenyl; or R$^4$ and R$^5$ taken together with the nitrogen to which they are attached represent a 5-6 member saturated ring comprising up to one other heteroatom selected from oxygen and nitrogen;

R$_6$ is
(1) a straight or branched chain alkyl group having 1-12 carbons;
(2) a straight or branched chain alkyl group having 1-12 carbons in which a hydrogen is substituted with a hydroxy, carboxylic acid or an alkyl ester having 1 to 4 carbons;
(3) a cycloalkyl group having 3 to 6 carbons;
(4) phenyl;
(5) OR$^7$, where R$^7$ is hydrogen, a alkali metal, a C$_{1-18}$ straight or branch chain alkyl group, a benzyl; and X is a halogen selected from the group consisting of chlorine, bromine and iodine.

2. The method of claim 1 wherein in said formula I and formula II compounds:

A is —CH=CH—;
R$_7$ is hydrogen; and
R is NH-t-butyl, sec-butyl, isopropyl, isobutyl, isopentyl or phenyl.

* * * * *

UNITED STATES PATENT AND TRADEMARK OFFICE
CERTIFICATE OF CORRECTION

PATENT NO. : 5,237,061
DATED : August 17, 1993
INVENTOR(S) : Apurba Bhattacharya, et al It is certified that error appears in the above-indentified patent and that said Letters Patent is hereby corrected as shown below:

Col. 10, lines 33-43, Claim 1, the portion of the formula reading

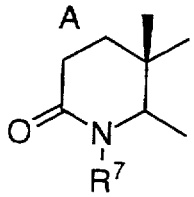   should read   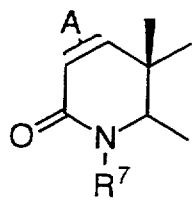 .

Col. 11, lines 6-16, Claim 1, the portion of the formula reading

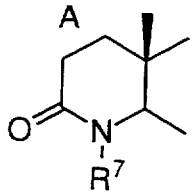   should read   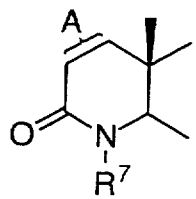 .

Signed and Sealed this

Tenth Day of January, 1995

Attest:

BRUCE LEHMAN

Attesting Officer   Commissioner of Patents and Trademarks